US009750395B2

(12) United States Patent
Taniguchi

(10) Patent No.: US 9,750,395 B2
(45) Date of Patent: Sep. 5, 2017

(54) INFORMATION MANAGEMENT APPARATUS AND CAPSULE ENDOSCOPE INSPECTION SYSTEM

(71) Applicant: OLYMPUS CORPORATION, Tokyo (JP)

(72) Inventor: Katsuyoshi Taniguchi, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 662 days.

(21) Appl. No.: 14/259,330

(22) Filed: Apr. 23, 2014

(65) Prior Publication Data
US 2014/0316193 A1 Oct. 23, 2014

Related U.S. Application Data

(63) Continuation of application No. PCT/JP2013/076954, filed on Oct. 3, 2013.

(30) Foreign Application Priority Data

Oct. 15, 2012 (JP) .................................. 2012-227898

(51) Int. Cl.
*A61B 1/04* (2006.01)
*A61B 1/00* (2006.01)
(Continued)

(52) U.S. Cl.
CPC ........ *A61B 1/00025* (2013.01); *A61B 1/0005* (2013.01); *A61B 1/00034* (2013.01);
(Continued)

(58) Field of Classification Search
CPC ............ A61B 1/00025; A61B 1/00034; A61B 1/00036; A61B 1/0005; A61B 1/00055; H02J 2007/0005
(Continued)

(56) References Cited

U.S. PATENT DOCUMENTS 6,494,827 B1 * 12/2002 Matsumoto ........ A61B 1/00032
600/117
7,615,006 B2 * 11/2009 Abe .................... A61B 1/00016
600/118
(Continued)

FOREIGN PATENT DOCUMENTS

JP 2005-304513 A 11/2005
JP 2005-312769 A 11/2005
(Continued)

OTHER PUBLICATIONS

International Search Report dated Nov. 26, 2013 from related International Application No. PCT/JP2013/076954.

*Primary Examiner* — Anhtuan T Nguyen
*Assistant Examiner* — Jae Woo
(74) *Attorney, Agent, or Firm* — Scully, Scott, Murphy & Presser, P.C.

(57) ABSTRACT

An information management apparatus that is used in a capsule endoscope inspection system including a receiving device operated by a built-in rechargeable battery and that is capable of communicating with the receiving device. The information management apparatus includes: a remaining battery capacity acquisition unit that acquires a current remaining capacity which is a remaining capacity of the battery; a storage unit that stores, for each examination item, a necessary remaining capacity which is a remaining capacity that the battery needs to complete an examination; a determination unit that compares the necessary remaining capacity corresponding to an examination item of a selected examination with the current remaining capacity; a calculation unit that, when the current remaining capacity is smaller than the necessary remaining capacity, calculates a charging time needed to increase the remaining capacity of the battery from the current remaining capacity to the necessary remaining capacity; and a control unit that, when (Continued)

the current remaining capacity is smaller than the necessary remaining capacity, causes a display device to display information on the charging time calculated by the calculation unit.

9 Claims, 12 Drawing Sheets

(51) Int. Cl.
    *A61B 5/07*     (2006.01)
    *A61B 5/06*     (2006.01)

(52) U.S. Cl.
    CPC ...... *A61B 1/00036* (2013.01); *A61B 1/00055* (2013.01); *A61B 1/00059* (2013.01); *A61B 1/041* (2013.01); *A61B 5/062* (2013.01); *A61B 5/073* (2013.01); *A61B 2560/0204* (2013.01)

(58) Field of Classification Search
    USPC .......................................................... 600/118
    See application file for complete search history.

(56) References Cited

U.S. PATENT DOCUMENTS

| | | | |
|---|---|---|---|
| 8,184,148 B2 | 5/2012 | Shigemori et al. | |
| 8,303,486 B2 | 11/2012 | Fujita | |
| 2002/0137987 A1* | 9/2002 | Watanabe | A61B 1/00105 600/178 |
| 2006/0178557 A1* | 8/2006 | Mintchev | A61B 1/041 600/104 |
| 2006/0220613 A1* | 10/2006 | Abe | A61B 1/00016 320/114 |
| 2007/0167715 A1* | 7/2007 | Shigemori | A61B 1/00016 600/407 |
| 2007/0260116 A1* | 11/2007 | Shigemori | A61B 1/00036 600/117 |
| 2007/0268280 A1* | 11/2007 | Fujita | A61B 1/00045 345/204 |
| 2008/0172255 A1* | 7/2008 | Hirakawa | G06F 19/321 705/3 |
| 2008/0232702 A1* | 9/2008 | Kimoto | A61B 1/041 382/232 |
| 2008/0306341 A1* | 12/2008 | Fujita | A61B 1/00022 600/118 |
| 2009/0018395 A1* | 1/2009 | Honda | A61B 1/00016 600/118 |
| 2009/0046821 A1* | 2/2009 | Shigemori | A61B 1/00016 375/371 |
| 2009/0076320 A1* | 3/2009 | Shigemori | A61B 1/00016 600/109 |
| 2009/0102917 A1* | 4/2009 | Minakuchi | A61B 1/00011 348/65 |
| 2009/0187077 A1* | 7/2009 | Hosoda | A61B 1/00034 600/178 |
| 2010/0022833 A1* | 1/2010 | Nagase | A61B 1/041 600/118 |
| 2010/0094104 A1* | 4/2010 | Nagase | A61B 1/041 600/302 |
| 2012/0112726 A1* | 5/2012 | Kaihori | A61B 1/041 323/299 |
| 2012/0271104 A1* | 10/2012 | Khait | A61B 1/041 600/109 |
| 2013/0066153 A1* | 3/2013 | McGrath | A61B 1/00034 600/188 |
| 2013/0158344 A1* | 6/2013 | Taniguchi | A61B 1/00016 600/103 |
| 2014/0081079 A1* | 3/2014 | Kawasaki | A61B 1/00009 600/103 |
| 2014/0163316 A1* | 6/2014 | Koide | A61B 1/00016 600/103 |
| 2015/0031954 A1* | 1/2015 | Kimoto | A61B 1/00006 600/118 |

FOREIGN PATENT DOCUMENTS

| | | | |
|---|---|---|---|
| JP | 2005304513 A | * | 11/2005 |
| JP | 2006-43109 A | | 2/2006 |
| JP | 2006-75300 A | | 3/2006 |
| JP | 2006-155242 A | | 6/2006 |
| JP | 2007-61302 A | | 3/2007 |
| JP | 2008-301953 A | | 12/2008 |

* cited by examiner

FIG.4

| EXAMINATION ID | |
|---|---|
| EXAMINATION EXECUTION INFORMATION | |
| EXAMINATION DATE AND TIME | YYYY/MM/DD |
| EXAMINATION ITEM | SMALL INTESTINE EXAMINATION |
| ⋮ | |
| PATIENT INFORMATION | |
| PATIENT ID | |
| PATIENT NAME | |
| SEX | |
| DATE OF BIRTH | |
| ⋮ | |
| ESTIMATED EXAMINATION TIME | 8:00:00 |
| NECESSARY REMAINING CAPACITY | ○○Ah |

FIG.5

| PATIENT ID | | | |
|---|---|---|---|
| PATIENT NAME | | | |
| SEX | | | |
| DATE OF BIRTH | | | |
| ⋮ | | | |
| EXAMINATION HISTORY | EXAMINATION DATE AND TIME | EXAMINATION ITEM | EXAMINATION TIME |
| | YYYY/MM/DD | SMALL INTESTINE EXAMINATION | 6:53:32 |
| | YYYY/MM/DD | SMALL INTESTINE EXAMINATION | XX:XX:XX |
| | ⋮ | ⋮ | ⋮ |

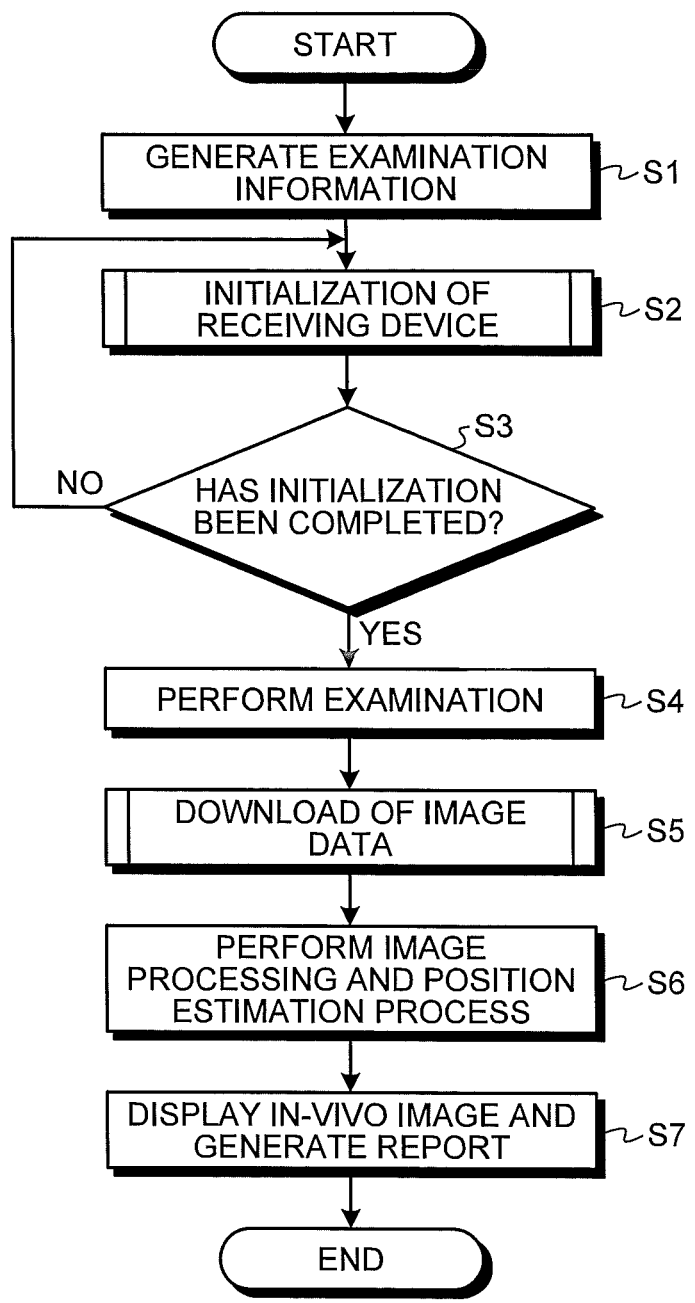

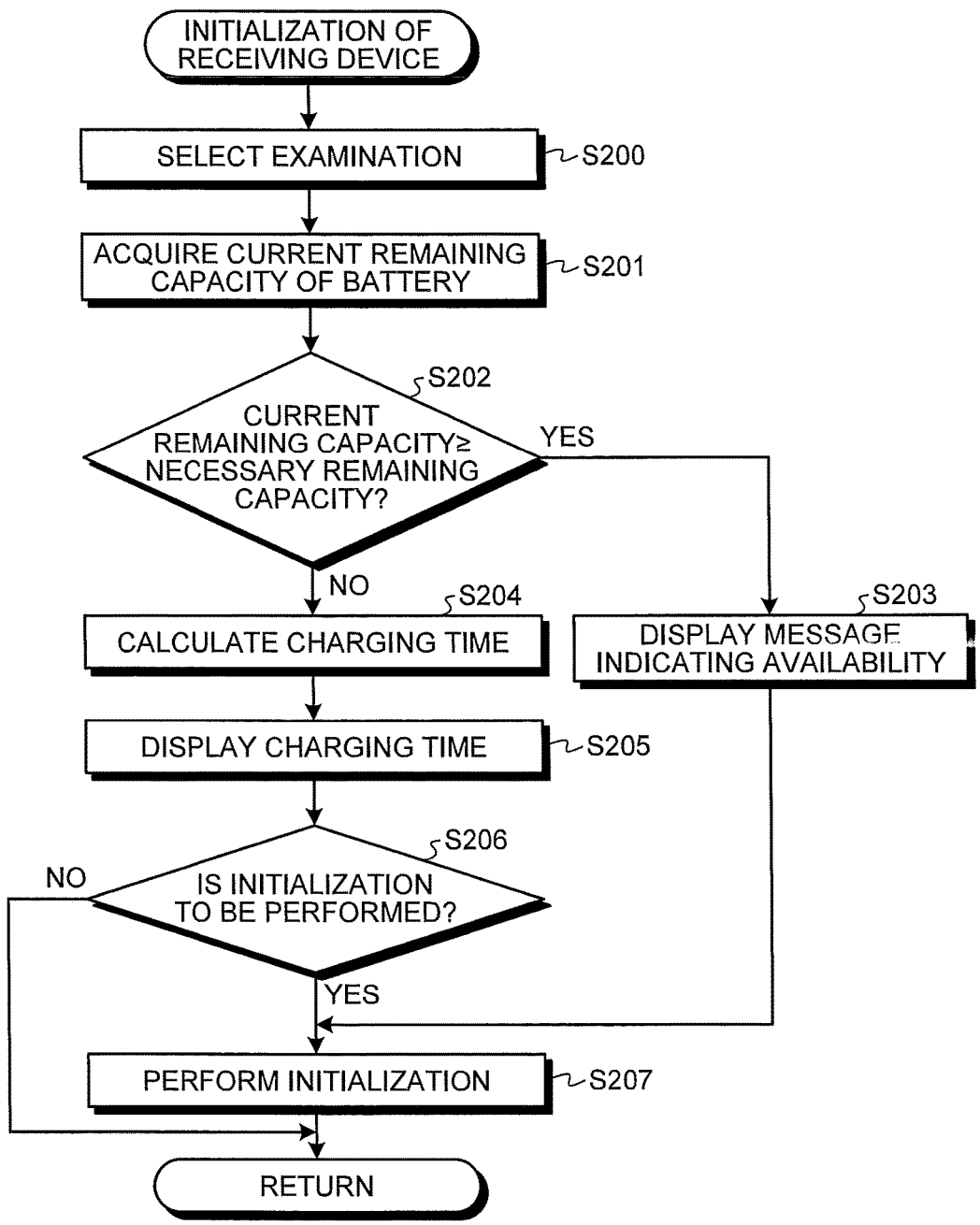

FIG.8

EXAMINATION SELECTION SCREEN (M1)

| EXAMINATION ID | PATIENT NAME | EXAMINA-TION ITEM | ... |
|---|---|---|---|
| ××××× | ... | ... | ... |
| ○○○○○ | ... | ... | ... |
| △△△△ | ... | ... | ... |
| ⋮ | ⋮ | ⋮ | ⋮ |

(m11)

m12 — [ CONFIRM ]

FIG.9

INITIALIZATION OF RECEIVING DEVICE (M2)

RECEIVING DEVICE 1

- m21 — INFO: IT MAY BE DIFFICULT TO COMPLETE SMALL INTESTINE EXAMINATION
- m22 — BATTERY CHARGING STATUS: 70 [%]
- m23 — CHARGING TIME NEEDED TO ENABLE SMALL INTESTINE EXAMINATION
- m24 — PREDICTED EXAMINATION AVAILABILITY RATE: SMALL INTESTINE 85 [%]

[ OK ] (m25)   [ CANCEL ] (m26)

INFORMATION MANAGEMENT APPARATUS AND CAPSULE ENDOSCOPE INSPECTION SYSTEM

CROSS REFERENCES TO RELATED APPLICATIONS

This application is a continuation of PCT international application Ser. No. PCT/JP2013/076954 filed on Oct. 3, 2013 which designates the United States, incorporated herein by reference, and which claims the benefit of priority from Japanese Patent Application No. 2012-227898, filed on Oct. 15, 2012, incorporated herein by reference.

BACKGROUND OF THE INVENTION

1. Field of the Invention

The present invention relates to an information management apparatus and a capsule endoscope inspection system for managing information in examinations using a capsule endoscope that is introduced into a subject and captures images of inside of the subject.

2. Description of the Related Art

In recent years, examinations using capsule endoscopes that are introduced into subjects and capture images of inside of the subjects are known in the field of endoscopes. A capsule endoscope is an apparatus that has a built-in imaging function, a built-in wireless communication function, and the like provided in a casing of a capsule shape formed in a size introducible into a digestive tract of a subject, and after being swallowed via a mouth of the subject, captures images while moving inside the digestive tract by peristaltic movement or the like and generates image data. The capsule endoscope sequentially and wirelessly transmits the generated image data to outside of the subject.

The image data wirelessly transmitted from the capsule endoscope is received by a receiving device provided outside the subject, and accumulated in a built-in memory or a portable memory. After the examination ends, the image data accumulated in the memory is transferred to an information processing apparatus, such as a workstation or a server, and subjected to specified image processing. A medical worker performs diagnosis on the subject by observing the images generated as described above.

The capsule endoscope is not able to move by itself, but is slowly moved by peristaltic movement of a digestive tract such as a small intestine. Therefore, for example, to observe the whole area of the small intestine, it normally takes at least 5 or 6 hours and it is difficult to control this time.

The receiving device is carried by the subject and is operated by a built-in rechargeable battery of the receiving device during the examination. Therefore, to prevent interruption of examinations due to empty charge in batteries, conventional receiving devices or information management apparatuses that register information or the like in the receiving devices are provided with functions to display remaining capacities of the batteries. In normal operation, a user uses a receiving device after he/she confirms that a battery is fully charged by using the above described function.

Furthermore, recent capsule endoscope inspection systems are provided with functions to determine whether receiving devices are able to operate for specified times at current remaining capacities of batteries and to display results of the determination (see, for example, Japanese Laid-open Patent Publication No. 2005-304513).

Moreover, chargeable capacities of rechargeable batteries are generally reduced with repeated charging and discharging, and therefore, available times in the fully charged states are gradually reduced. Therefore, some receiving devices are provided with functions to restrict use of receiving devices according to the number of times of charging and discharging, or functions to measure voltages in fully charged states and estimate whether operation for specified times are possible.

SUMMARY OF THE INVENTION

An information management apparatus according to one aspect of the invention is used in a capsule endoscope inspection system including a receiving device operated by a built-in rechargeable battery and that is capable of communicating with the receiving device. The information management apparatus includes: a remaining battery capacity acquisition unit that acquires a current remaining capacity which is a remaining capacity of the battery; a storage unit that stores, for each examination item, a necessary remaining capacity which is a remaining capacity that the battery needs to complete an examination; a determination unit that compares the necessary remaining capacity corresponding to an examination item of a selected examination with the current remaining capacity; a calculation unit that, when the current remaining capacity is smaller than the necessary remaining capacity, calculates a charging time needed to increase the remaining capacity of the battery from the current remaining capacity to the necessary remaining capacity; and a control unit that, when the current remaining capacity is smaller than the necessary remaining capacity, causes a display device to display information on the charging time calculated by the calculation unit.

A capsule endoscope inspection system according to another aspect of the invention includes: a capsule endoscope that is configured to be introduced into a subject and captures an image of inside of the subject; a receiving device operated by a built-in rechargeable battery; and an information management apparatus capable of communicating with the receiving device. The information management apparatus includes: a remaining battery capacity acquisition unit that acquires a current remaining capacity which is a remaining capacity of the battery; a storage unit that stores, for each examination item, a necessary remaining capacity which is a remaining capacity that the battery needs to complete an examination; a determination unit that compares the necessary remaining capacity corresponding to an examination item of a selected examination with the current remaining capacity; a calculation unit that, when the current remaining capacity is smaller than the necessary remaining capacity, calculates a charging time needed to increase the remaining capacity of the battery from the current remaining capacity to the necessary remaining capacity; and a control unit that, when the current remaining capacity is smaller than the necessary remaining capacity, causes a display device to display information on the charging time calculated by the calculation unit.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 4 is a table illustrating an example of contents of examination information stored in an examination information storage unit illustrated in FIG. 3;

FIG. 5 is a table illustrating an example of contents of patient information stored in a patient information storage unit illustrated in FIG. 1;

FIG. 6 is a flowchart illustrating a series of processes related to a capsule endoscopic examination;

FIG. 7 is a flowchart illustrating a process of initializing the receiving device, which is performed by the information management apparatus illustrated in FIG. 3;

FIG. 8 is a schematic diagram illustrating an example of an examination selection screen;

FIG. 9 is a schematic diagram illustrating an example of an initialization confirmation screen;

DETAILED DESCRIPTION OF THE PREFERRED EMBODIMENTS

Exemplary embodiments of an information management apparatus and a capsule endoscope inspection system according to the present invention will be described below with reference to the drawings. The present invention is not limited by the embodiments below. Furthermore, in describing the drawings, the same components are denoted by the same reference signs.

First Embodiment

Figure 1:
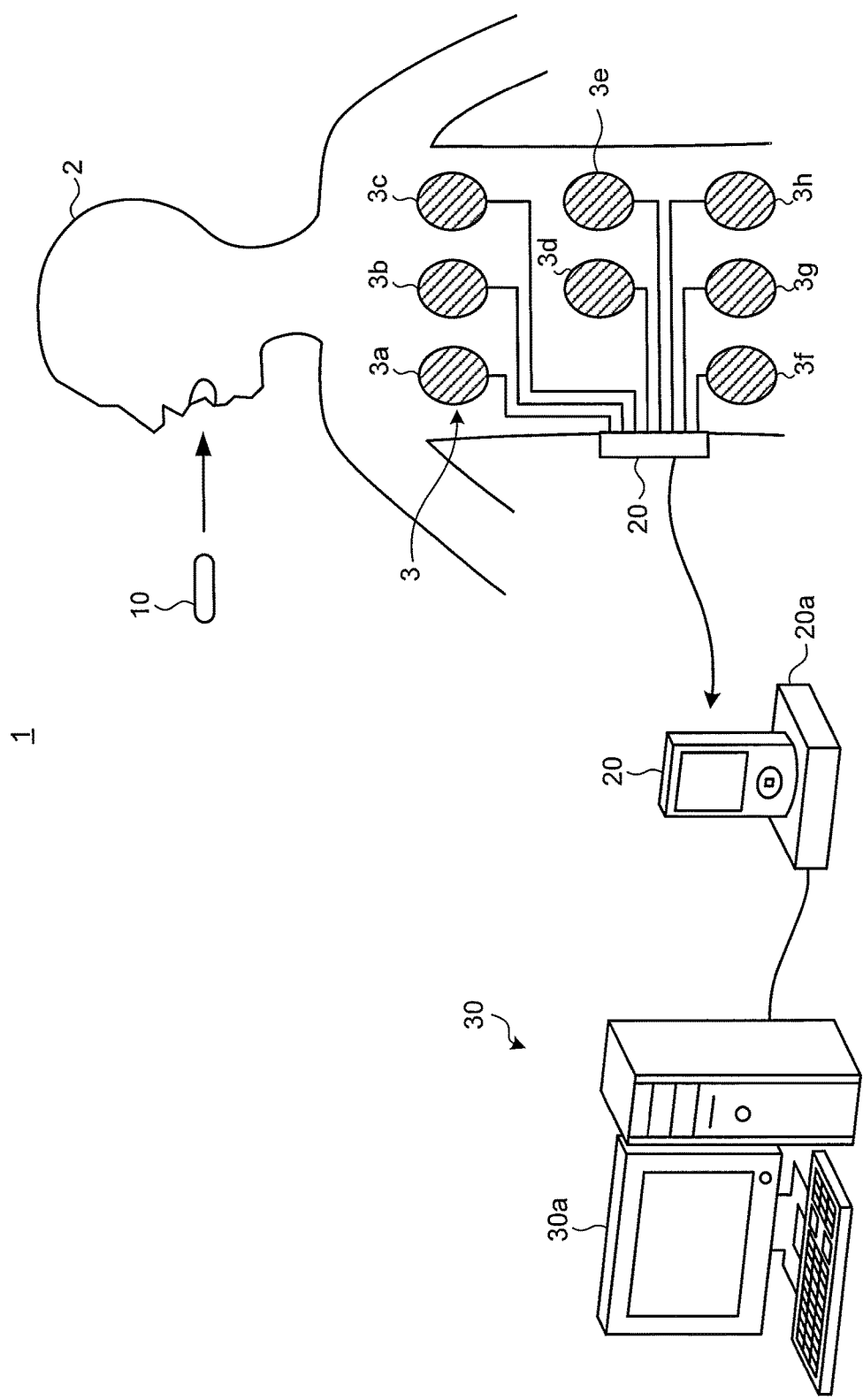
FIG. 1 is a schematic diagram illustrating a schematic configuration of a capsule endoscope inspection system according to a first embodiment of the present invention.

FIG. 1 is a schematic diagram illustrating a schematic configuration of a capsule endoscope inspection system according to a first embodiment of the present invention. As illustrated in FIG. 1, a capsule endoscope inspection system 1 according to the first embodiment includes: a capsule endoscope 10 that is introduced into a subject 2, that captures an image of inside of the subject 2 to generate image data, and that transmits the image data by superimposing the image data on a wireless signal; a receiving device 20 that receives the wireless signal transmitted from the capsule endoscope 10 via a receiving antenna unit 3 attached to the subject 2; and an information management apparatus 30 that manages information on capsule endoscopic examinations.

Figure 2:
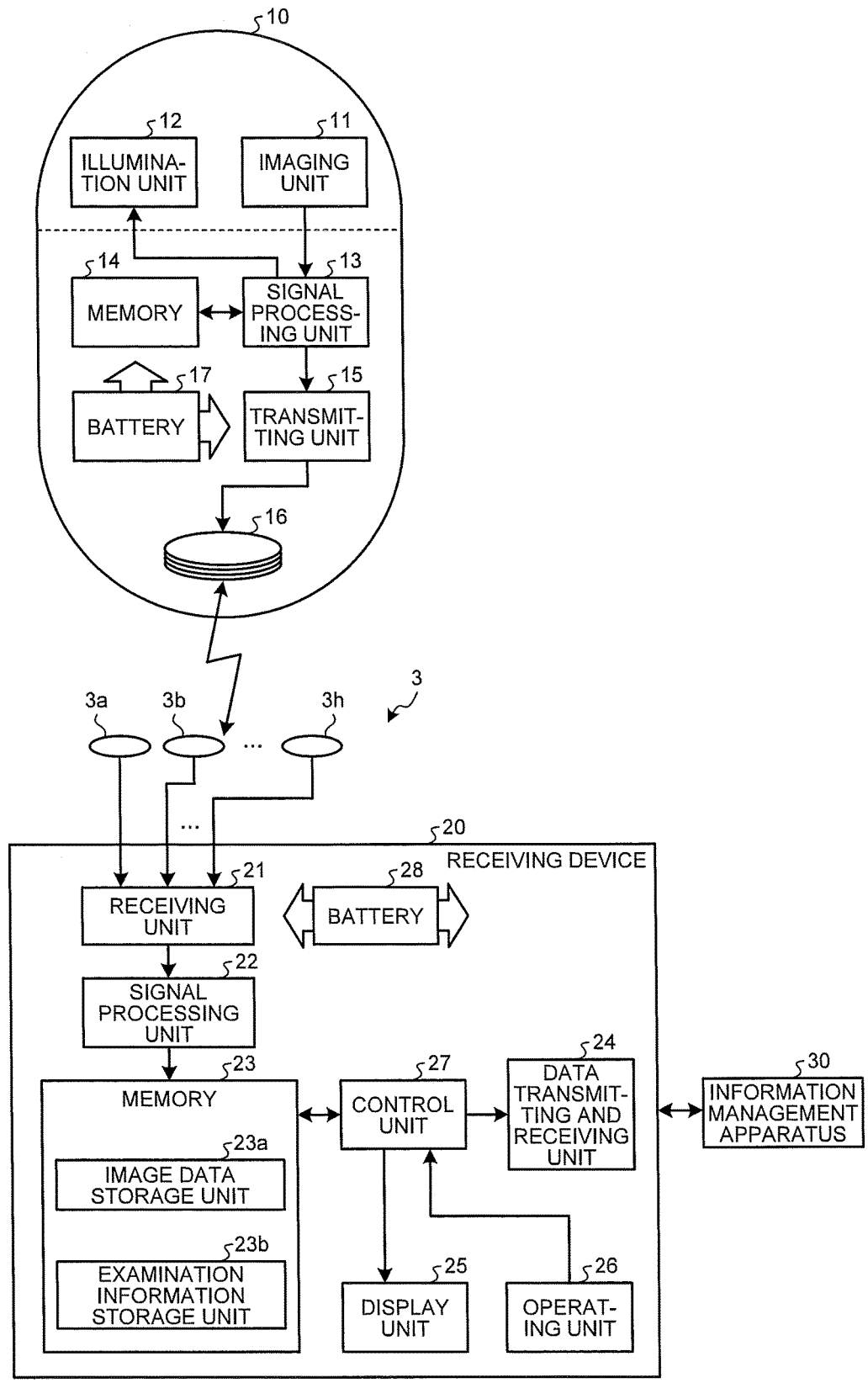
FIG. 2 is a diagram illustrating a schematic configuration of a capsule endoscope and a receiving device illustrated in FIG. 1.

FIG. 2 is a diagram illustrating schematic configurations of the capsule endoscope 10 and the receiving device 20.

The capsule endoscope 10 is a device that has various built-in parts, such as an imaging element, in a capsule shaped casing of a size swallowable by the subject 2, and includes: an imaging unit 11 that captures an image of the inside of the subject 2; an illumination unit 12 that illuminates the inside of the subject 2; a signal processing unit 13; a memory 14; a transmitting unit 15 and an antenna 16; and a battery 17.

The imaging unit 11 includes, for example: an imaging element, such as a CCD or a CMOS, which generates and outputs an imaging signal representing the inside of the subject 2 based on an optical image formed on a light receiving surface; and an optical system, such as an objective lens, which is arranged on a light receiving surface side of the imaging element.

The illumination unit 12 is realized by a light emitting diode (LED) or the like that emits light toward the inside of the subject 2 when an image is captured.

The capsule endoscope 10 has a built-in circuit board (not illustrated) in which a driving circuit or the like that drives each of the imaging unit 11 and the illumination unit 12 is formed. The imaging unit 11 and the illumination unit 12 are fixed on the circuit board such that respective fields of view are directed outward from one end portion of the capsule endoscope 10.

The signal processing unit 13 controls each unit in the capsule endoscope 10, performs A/D conversion on an imaging signal output from the imaging unit 11 to generate digital image data, and further performs specified signal processing on the digital image data.

The memory 14 temporarily stores various operation executed by the signal processing unit 13 and the image data subjected to the signal processing in the signal processing unit 13.

The transmitting unit 15 and the antenna 16 superimpose, together with related information, the image data stored in the memory 14 on the wireless signal and transmits the superimposed signal to outside.

The battery 17 supplies electric power to each unit in the capsule endoscope 10. The battery 17 includes a power supply circuit that performs boosting or the like of electric power supplied from a primary battery or secondary battery, such as a button battery.

After being swallowed by the subject 2, the capsule endoscope 10 sequentially captures images of living body sites (an esophagus, a stomach, a small intestine, a large intestine, and the like) at specified time intervals (for example, 0.5 second time interval) while moving inside the digestive tract of the subject 2 by peristaltic movement or the like of organs. The image data and related information generated by the imaging operation are sequentially and wirelessly transmitted to the receiving device 20. The related information includes identification information (for example, a serial number) or the like assigned in order to individually identify the capsule endoscope 10.

The receiving device 20 receives the image data and the related information wirelessly transmitted from the capsule endoscope 10 via the receiving antenna unit 3 including a plurality of receiving antennas 3a to 3h (eight receiving antennas in FIG. 1). Each of the receiving antennas 3a to 3h is realized by using a loop antenna or a dipole antenna for example, and arranged at a specified position on an outside surface of a body of the subject 2.

As illustrated in FIG. 2, the receiving device 20 includes: a receiving unit 21; a signal processing unit 22; a memory 23; a data transmitting and receiving unit 24; a display unit 25; an operating unit 26; a control unit 27 that controls each of the above units; and a battery 28 that supplies electric power to each of the above units.

The receiving unit 21 receives the image data wirelessly transmitted from the capsule endoscope 10 via the receiving antennas 3a to 3h.

The signal processing unit 22 performs specified signal processing on the image data received by the receiving unit 21.

The memory 23 includes: an image data storage unit 23a that stores the image data subjected to the signal processing by the signal processing unit 22 and related information on this image data; and an examination information storage unit 23b that stores examination information received from the information management apparatus 30.

The data transmitting and receiving unit 24 is an interface connectable to a USB or a communication line, such as a wired LAN or a wireless LAN, receives various types of information, such as the examination information, from the information management apparatus 30, and transmits the image data and the related information stored in the memory 23 to the information management apparatus 30 under control of the control unit 27.

The display unit 25 displays the examination information, an in-vivo image based on image data acquired during a capsule endoscopic examination (hereinafter, may be simply described as an examination), or the like based on instruction information or the like input via the operating unit 26. The function to play back and display, on the receiving device 20, the in-vivo image acquired during the examination may be described as a playback view.

The operating unit 26 is an input device used by a user to input various setting information or instruction information to the receiving device 20. The operating unit 26 receives, for example, input of in-vivo image capturing operation performed by the user while the playback view is being performed.

The receiving device 20 is attached to and carried by the subject 2 while the capsule endoscope 10 is capturing images (for example, while the capsule endoscope 10 is passing through the digestive tract after the capsule endoscope 10 is swallowed by the subject 2 and until the capsule endoscope 10 is excreted). During this period, the receiving device 20 adds, to the image data received via the receiving antenna unit 3, related information, such as receiving intensity information and receiving time information, on each of the receiving antennas 3a to 3h, and stores the image data and the related information in the image data storage unit 23a.

The battery 28 is charged by setting the receiving device 20 in a cradle 20a and connecting the cradle 20a to a power supply.

After the capsule endoscope 10 completes the image capturing, the receiving device 20 is removed from the subject 2, is then connected to the information management apparatus 30, and transfers (downloads) the image data and the related information stored in the image data storage unit 23a to the information management apparatus 30. In FIG. 1, the cradle 20a is connected to a USB port of the information management apparatus 30, and by setting the receiving device 20 in the cradle 20a, the receiving device 20 is connected to the information management apparatus 30.

The information management apparatus 30 is configured by using, for example, a workstation including a display device 30a, such as a CRT display or a liquid crystal display. The information management apparatus 30 registers the examination information on an examination of the subject 2 in the receiving device 20, performs specified processing on image data transferred from the receiving device 20, and generates observation image used for medical diagnosis on the subject 2.

Figure 3:
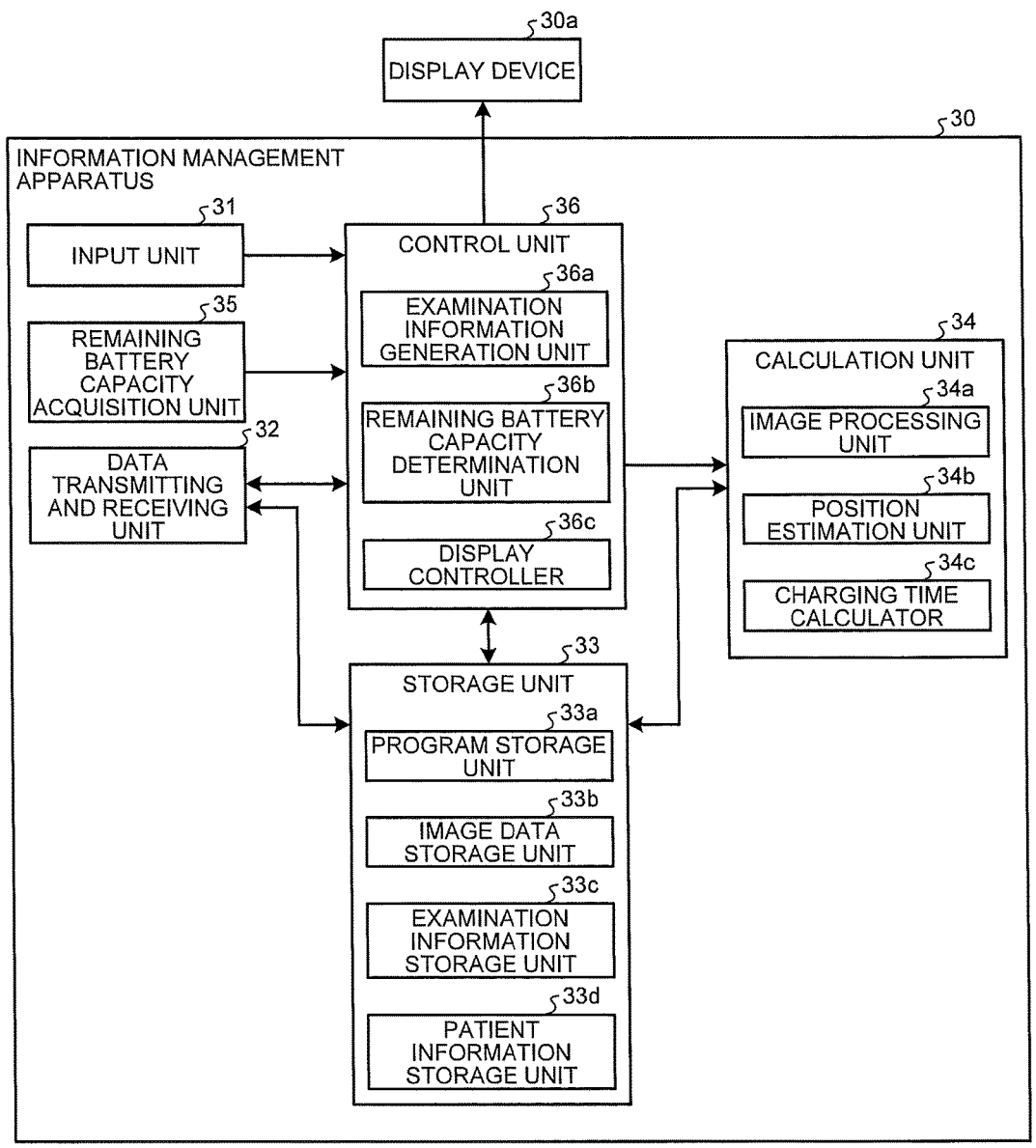
FIG. 3 is a block diagram illustrating a schematic configuration of an information management apparatus illustrated in FIG. 1.

FIG. 3 is a block diagram illustrating a schematic configuration of the information management apparatus 30. As illustrated in FIG. 3, the information management apparatus 30 includes: an input unit 31; a data transmitting and receiving unit 32; a storage unit 33; a calculation unit 34; a remaining battery capacity acquisition unit 35; and a control unit 36 that integrally controls each of the above units.

The input unit 31 is realized by an input device, such as a keyboard, a mouse, a touch panel, or various switches. The input unit 31 receives input of information and instructions according to user's operation.

The data transmitting and receiving unit 32 is an interface connectable to a USB or a communication line, such as a wired LAN or a wireless LAN, and includes a USB port or a LAN port. In the first embodiment, the data transmitting and receiving unit 32 is connected to the receiving device 20 via the cradle 20a connected to the USB port, and transmits and receives data to and from the receiving device 20.

The storage unit 33 is realized by a semiconductor memory such as a flash memory, a RAM, or a ROM, or by a recording medium such as an HDD, an MO, a CD-R, or a DVD-R and a read and write device or the like that reads and writes information from and to the recording medium. The storage unit 33 includes: a program storage unit 33a that stores programs and various types of information for causing the information management apparatus 30 to operate and execute various functions; an image data storage unit 33b that stores the image data and the related information acquired via the receiving device 20; and a patient information storage unit 33d that accumulates information related to a patient that is the subject 2.

FIG. 4 is a table illustrating an example of contents of the examination information stored in an examination information storage unit 33c. As illustrated in FIG. 4, the examination information contains an examination ID uniquely assigned to each examination, examination execution information such as an examination date and time and an examination item, patient information such as a patient ID, a patient name, sex, and a date of birth, an estimated examination time that is estimated according to the examination item, and a remaining capacity (necessary remaining capacity) of the battery 28 needed to complete an examination corresponding to the estimated examination time. Of these pieces of information, the examination item indicates a type of an examination for each organ to be examined (for example, a stomach examination, a small intestine examination, or a large intestine examination). The estimated examination time is a time from when the capsule endoscope 10 is swallowed by the subject 2 to when it passes through an examination area corresponding to the examination item. For example, when the examination item is the small intestine examination, the estimated examination time is a time from when the capsule endoscope 10 is swallowed to when it passes through the whole area of the small intestine, that is, to when it enters a large intestine area. In the estimated examination time, a statistically calculated general value (for example, 8 hours for the small intestine examination) is set as an initial value. The necessary remaining capacity is a remaining capacity needed for the receiving device 20 to continue operation during the above described estimated examination time, is calculated based on the estimated examination time, and is stored for each examination item.

FIG. 5 is a table illustrating an example of contents of the patient information stored in the patient information storage unit 33d. As illustrated in FIG. 5, the patient information contains personal information on a patient such as a patient ID assigned to each patient, a patient name, sex, and a date of birth, and an examination history such as an examination date and time, an examination item, and an examination time. The examination time is a time taken to complete an examination of an examination area corresponding to the examination item, and when the examination item is the small intestine examination for example, corresponds to a time from when the capsule endoscope 10 is swallowed to when it passes through the whole area of the small intestine.

The calculation unit 34 is realized by hardware, such as a CPU, and by reading a specified program stored in the program storage unit 33a, performs a specified calculation process based on the information input via the input unit 31.

More specifically, the calculation unit 34 includes: an image processing unit 34a; a position estimation unit 34b; and a charging time calculator 34c. The image processing unit 34a performs specified image processing on the image data stored in the image data storage unit 33b. More specifically, the image processing unit 34a performs image processing, such as a white balance process, demosaicing, color conversion, density conversion (gamma conversion or the like), smoothing (noise elimination or the like), or sharpening (edge enhancement or the like), on the image data stored in the image data storage unit 33b to thereby generate image data to be displayed, and performs image processing, such as an average color calculation process, a lesion detection process, a red detection process, or an organ detection process, as a specified support for diagnosis.

The position estimation unit 34b estimates, based on the receiving intensity information or the receiving time information on each of the receiving antennas 3a to 3h as the related information on the image data, positions of the capsule endoscope 10 at a timing at which the receiving device 20 receives a wireless signal containing the image data, generates positional information, and calculates a movement trajectory of the capsule endoscope 10 inside the subject 2 by connecting temporally successive positions of the capsule endoscope 10 based on the positional information.

The charging time calculator 34c calculates a charging time of the receiving device 20 needed to perform the examination with respect to the examination information stored in the examination information storage unit 33c. A method of calculating the charging time will be described later.

The remaining battery capacity acquisition unit 35 detects a voltage value of the battery 28 when the receiving device 20 is connected to the information management apparatus 30 via the cradle 20a, and acquires a remaining capacity at this time as information on the charging status of the receiving device 20.

The control unit 36 is realized by hardware, such as a CPU, and by reading various programs stored in the storage unit 33, transfers instructions or data to each unit of the information management apparatus 30 based on signals input via the input unit 31, image data input from the data transmitting and receiving unit 32, or the like, and integrally controls the entire operation of the information management apparatus 30.

More specifically, the control unit 36 includes: an examination information generation unit 36a; a remaining battery capacity determination unit 36b; and a display controller 36c. The examination information generation unit 36a generates the examination information based on the information input via the input unit 31. The remaining battery capacity determination unit 36b determines whether a remaining capacity of the battery 28 is enough for an examination to be performed, when the receiving device 20 is connected to the information management apparatus 30 via the cradle 20a. The display controller 36c displays various types of information, an in-vivo image processed by the image processing unit 34a, or the like in a specified format on the display device 30a based on the information input via the input unit 31, a result of determination by the remaining battery capacity determination unit 36b, or the like.

Operation of the capsule endoscope inspection system 1 will be described below. FIG. 6 is a flowchart illustrating a series of processes related to a capsule endoscopic examination.

First, at Step S1, the information management apparatus 30 generates examination information based on an examination order input by a user via the input unit 31. More specifically, when the user performs operation of inputting each item of the examination information illustrated in FIG. 5 by using the input unit 31, the examination information generation unit 36a generates new examination information and stores the generated examination information in the examination information storage unit 33c.

At subsequent Step S2, the information management apparatus 30 initializes the receiving device 20. The initialization of the receiving device 20 is a process of deleting information that has been stored in the receiving device 20 and register examination information on an examination to be performed next. The initialization of the receiving device 20 is started by connecting the cradle 20a to the information management apparatus 30 and setting the receiving device 20 in the cradle 20a.

FIG. 7 is a flowchart illustrating a process of initializing the receiving device 20, which is performed by the information management apparatus 30. When the receiving device 20 is set in the cradle 20a and the information management apparatus 30 recognizes the receiving device 20, at Step S200, the information management apparatus 30 selects an examination to be registered in the receiving device 20. More specifically, the display controller 36c first displays an examination selection screen M1 as illustrated in FIG. 8 on the display device 30a for example. The examination selection screen M1 contains an examination display area m11 for displaying a list of examinations that have not been performed, and a confirmation button m12. When the user selects a desired examination in the examination display area m11 by performing specified pointer operation (for example, click operation) on the examination selection screen M1 by using the input unit 31 and then selects the confirmation button m12, a signal representing the selected examination is input to the control unit 36. In response to this, the control unit 36 reads examination information related to the selected examination from the examination information storage unit 33c.

At Step S201, the remaining battery capacity acquisition unit 35 acquires a remaining capacity (current remaining capacity) of the battery 28 of the receiving device 20 at this time.

At subsequent Step S202, the remaining battery capacity determination unit 36b acquires a necessary remaining capacity of the battery 28 from the examination information (see FIG. 4), and determines whether the current remaining capacity is equal to or greater than the necessary remaining capacity. For example, when the examination item is the small intestine examination, it is determined whether a charging status indicates that operation for 8 hours, which is a statistically calculated estimated examination time, is possible.

As a result of the determination by the remaining battery capacity determination unit 36b, if the current remaining capacity is equal to or greater than the necessary remaining capacity (Step S202: Yes), the display controller 36c displays, on the display device 30a, a message or the like indicating that the receiving device 20 is available (Step S203).

Subsequently, at Step S207, the information management apparatus 30 initializes the receiving device 20. That is, information that has been stored in the memory 23 of the receiving device 20 is deleted, and the examination information is transmitted to the receiving device 20 via the data transmitting and receiving unit 32 and is stored in the examination information storage unit 23b.

In contrast, if the current remaining capacity is smaller than the necessary remaining capacity (Step S202: No), the charging time calculator 34c calculates a necessary charging time needed to increase the remaining capacity of the battery 28 to the necessary remaining capacity (Step S204).

At subsequent Step S205, the display controller 36c displays the calculated charging time on the display device 30a. FIG. 9 is a schematic diagram illustrating an example of an initialization confirmation screen displayed at this time. An initialization confirmation screen M2 illustrated in FIG. 9 contains an information display field m21, a charging status display field m22, a charging time display field m23, a predicted examination availability rate display field m24, an OK button m25, and a cancel button m26.

The information display field m21 is an area for displaying information indicating a state of the receiving device 20. For example, a message is displayed to indicate that it may be difficult to complete a designated examination (for example, a small intestine examination) in the current charging status and to call attention of a user.

The charging status display field m22 is an area for displaying, as a current charging status of the battery 28, a rate (for example, 70%) of the current remaining capacity with respect to the necessary remaining capacity.

The charging time display field m23 is an area for displaying the charging time calculated at Step S204. In FIG. 9, as an example, it is indicated that charging for 23 minutes and 15 seconds is needed to enable the examination of a small intestine area.

The predicted examination availability rate display field m24 is an area for displaying a predicted value of a rate of an area that can be examined in the current charging status. In FIG. 9, as an example, it is indicated that 85% of the whole area of the small intestine can be examined.

The user determines whether to initialize the receiving device 20 by referring to the information, such as the charging time, displayed on the initialization confirmation screen M2, and inputs a result of the determination to the information management apparatus 30. Specifically, an instruction signal for performing initialization is input to the information management apparatus 30 by pointer operation (for example, click operation) on the OK button m25 by using the input unit 31. Conversely, an instruction signal for cancelling initialization is input to the information management apparatus 30 by pointer operation (the same as above) on the cancel button m26. If the user wants to start the examination in a state in which the battery 28 is fully charged, it is preferable to click the OK button m25 after a wait for a time displayed in the charging time display field m23. Alternatively, if the user determines that 85% of the whole area of the small intestine is enough as an examination available area, it is preferable to immediately click the OK button m25. In contrast, if the user stops using the receiving device 20, it is preferable to click the cancel button m26.

The receiving device 20 is continuously charged while being set in the cradle 20a; therefore, information displayed in each of the display fields m21 to m24 is updated as needed. Alternatively, it may be possible to perform screen settings such that information displayed in each of the display fields m21 to m24 is updated at a timing at which the initialization confirmation screen M2 is displayed.

At Step S206, the control unit 36 confirms the instruction signal on initialization input from the input unit 31. If the instruction signal for cancelling initialization is input (Step S206: No), the receiving device 20 is not initialized and the process returns to the main routine. In contrast, if the instruction signal for performing initialization is input (Step S206: Yes), the process proceeds to Step S207. Thereafter, the process returns to the main routine.

At Step S3 subsequent to Step S2, if the receiving device 20 has already been initialized (Step S3: Yes), the process proceeds to Step S4. In contrast, if the receiving device 20 has not been initialized (Step S3: No), the receiving device 20 is charged or another receiving device 20 is prepared, and the process returns to Step S2.

At Step S4, the examination using the capsule endoscope 10 is performed on the subject 2. Specifically, the receiving antenna unit 3 is attached to the subject 2, the initialized receiving device 20 is carried by the subject 2, and the capsule endoscope 10 is swallowed by the subject 2. Accordingly, the capsule endoscope 10 captures images while moving inside the subject 2 and sequentially transmits image data to the receiving device 20.

In this case, the receiving device 20 may display, on the display unit 25, a playback view of in-vivo images based on the image data received from the capsule endoscope 10. During this period, if in-vivo image capturing operation is performed on the operating unit 26, the control unit 27 adds, to an in-vivo-image being displayed, a flag indicating that the capturing is performed.

When the examination ends, the user removes the receiving device 20 from the subject 2 and downloads the image data (Step S5). Download of the image data is started when the receiving device 20 is set in the cradle 20a connected to the information management apparatus 30.

At Step S6, the image processing unit 34a performs specified image processing on the image data stored in the image data storage unit 33b. The position estimation unit 34b estimates positions of the capsule endoscope 10 at timings at which the in-vivo images are captured based on the related information on the image data, and acquires a movement trajectory of the capsule endoscope 10 inside the subject 2 by connecting these positions. The image data subjected to the image processing and the information on the positions and the trajectory of the capsule endoscope 10 are stored in the image data storage unit 33b. In this case, the calculation unit 34 may detect boundaries of organs based on a result of an organ detection process, and may store, in the examination information storage unit 23b, a time (examination time) taken by the capsule endoscope 10 to pass through a boundary of an organ (for example, a small intestine) corresponding to the examination item.

Figure 10:
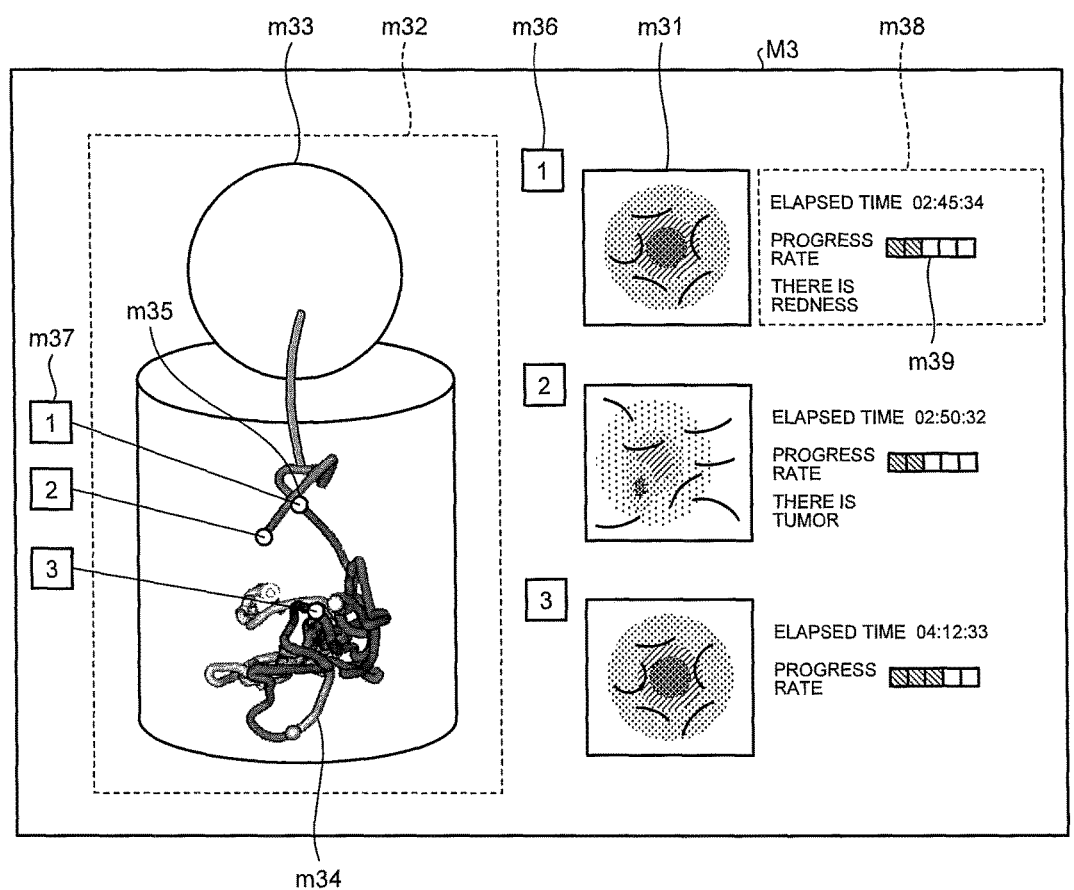
FIG. 10 is a schematic diagram illustrating an example of an in-vivo image display screen.

At Step S7, the display controller 36c displays, on the display device 30a, in-vivo images based on the image data subjected to the image processing. FIG. 10 is a schematic diagram illustrating an example of an in-vivo image display screen. A screen M3 illustrated in FIG. 10 contains multiple in-vivo images m31 captured while the playback view is being performed in the receiving device 20, and a trajectory display area m32 for displaying a movement trajectory of the capsule endoscope 10 estimated by the position estimation unit 34b. In the trajectory display area m32, a subject image m33 representing the subject 2 and a trajectory m34 superimposed on the subject image m33 are displayed three dimensionally. It may be possible to display parts of the trajectory m34 in different colors in accordance with organs appearing in the in-vivo images based on the result of the organ detection process performed by the image processing unit 34a.

On the trajectory m34, markers m35 indicating the positions of the respective captured in-vivo images m31 are displayed. Furthermore, an image number m36 indicating the order of capturing is added to each of the in-vivo images m31. Moreover, number displays m37 that are the same as the image numbers m36 are displayed near the trajectory display area m32, and the number displays m37 are linked to the corresponding markers m35 by lines. The number displays m37 may be arranged outside the trajectory display area m32 as illustrated in FIG. 10, or may be arranged near the corresponding markers m35 inside the trajectory display area m32.

An image information field m38 for displaying information on each of the in-vivo images m31 is provided near each of the in-vivo images m31. In the image information field m38, an elapsed time from when the capsule endoscope 10 is swallowed by the subject 2 to when the in-vivo image m31 is captured, a progress rate of the in-vivo image m31 with respect to the examination area, remarks such as "there is redness", "there is a tumor", and the like are displayed. The progress rate is calculated as an elapsed time for each of the in-vivo images m31 with respect to the time taken from when the capsule endoscope 10 is swallowed to when it passes through the examination area (for example, a small intestine). In FIG. 10, the progress rate is indicated by an indicator m39; however, for example, the progress rate may be displayed by letters such as "20%". The remarks may be input manually by the user, or a result of a lesion detection process performed by the image processing unit 34a may be displayed automatically. The image numbers m36 may be displayed inside the image information field m38.

Figure 11:
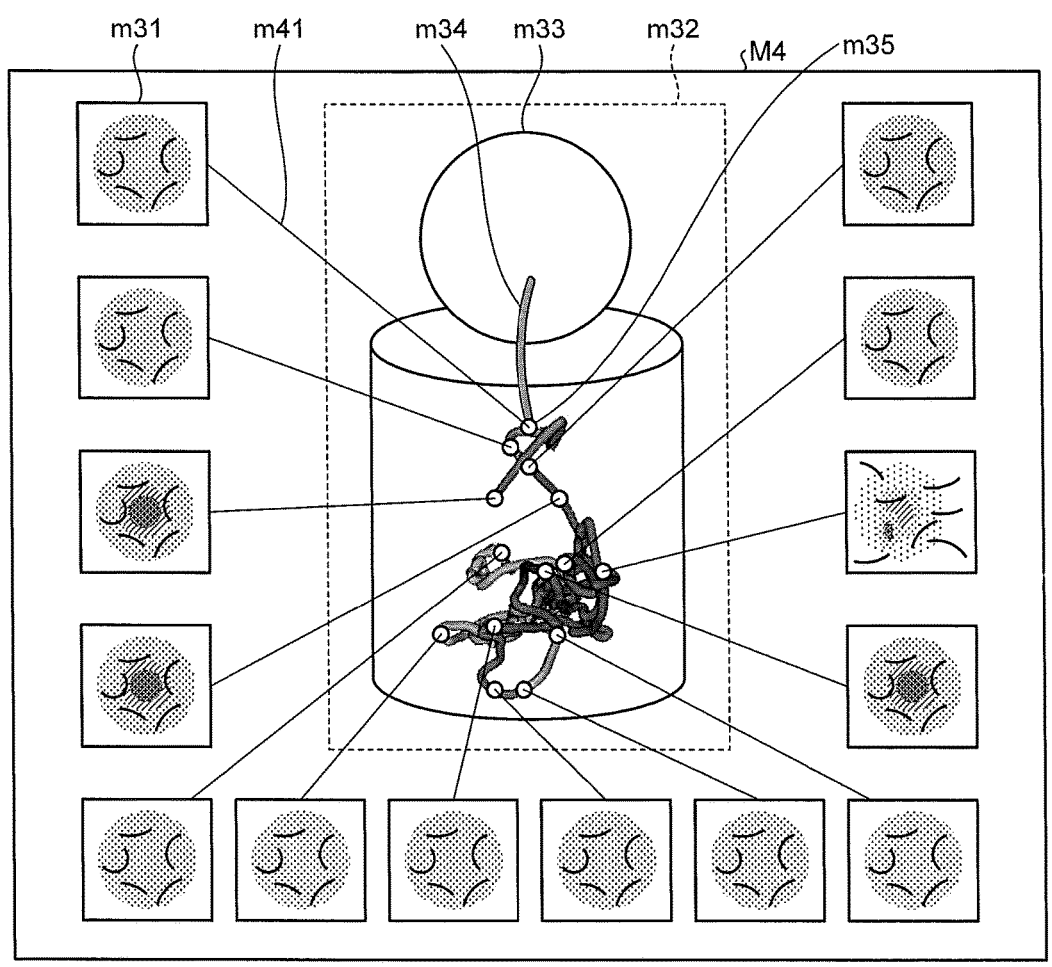
FIG. 11 is a schematic diagram illustrating another example of the in-vivo image display screen.

FIG. 11 is a schematic diagram illustrating another example of the in-vivo image display screen. In a screen M4 illustrated in FIG. 11, the trajectory display area m32 is arranged in the approximate center of the screen M4, and the captured in-vivo images m31 are arranged along three sides of the screen M4 so as to surround the trajectory display area m32. The in-vivo images m31 are directly linked to the respective markers m35 on the trajectory m34 by connection lines m41. Alternatively, as a modified example of FIG. 11, it may be possible to arrange the number displays m37 corresponding to the respective image numbers m36 illustrated in FIG. 10, instead of the in-vivo images m31, around the trajectory display area m32, and link the number displays m37 to the respective markers m35 by the connection lines m41.

As one of the purposes of the capsule endoscopic examination, it is determined whether an endoscope for treatment that is performed according to a result of diagnosis is introduced via a mouth or an anus. Therefore, it is necessary to estimate a position of an in-vivo image in which an abnormality seems to be found as a result of the examination (hereinafter, this image is described as a finding image). However, conventionally, even when multiple finding images are extracted from a series of in-vivo images, positional information on each of the finding images is individually displayed for each finding image, and it is difficult to determine a positional relationship of the finding images. Furthermore, an imaging time may be used as information indicating the positional relationship of the finding images; however, with use of the imaging time, it is very difficult to intuitively determine the positional relationship.

In contrast, as illustrated in FIG. 10 and FIG. 11, by displaying the multiple captured in-vivo images m31 and the trajectory display area m32 in a single screen and connecting the in-vivo images m31 and the markers m35 directly or indirectly, it becomes possible for the user to intuitively recognize the positional relationship of the in-vivo images m31. Furthermore, as illustrated in FIG. 10 and FIG. 11, although the capsule endoscope 10 moves in a complex manner inside the subject 2, the user is able to easily recognize what position in the examination area is represented by each of the in-vivo images m31 because the progress rate is displayed near each of the in-vivo images m31.

The user observes the in-vivo images displayed on the display device 30a as described above, and generates a report by appropriately attaching the captured images.

Thus, the series of the processes on the capsule endoscopic examination is completed.

As described above, according to the first embodiment, the charging status of the battery 28 is confirmed when the receiving device 20 is to be initialized, and it is determined whether a necessary remaining capacity to complete an examination is ensured. If the necessary remaining capacity is not ensured, an alert is displayed for the user. Therefore, it becomes possible to prevent interruption of the examination due to empty charge in the battery 28. In contrast, if the necessary remaining capacity is ensured, information on this condition is displayed. Therefore, the user need not perform unnecessary charging operation, and is able to prevent delays in starting examinations.

Furthermore, according to the first embodiment, a charging time is displayed that is needed to increase the remaining capacity of the battery 28 to a level at which the examination can be completed. Therefore, the user becomes able to efficiently perform examinations by recognizing a wait time, modifying examination schedules, or the like.

Moreover, according to the first embodiment, a rate of an area that can be examined at a current remaining capacity is displayed in addition to the above described charging status and charging time of the battery 28. Therefore, the user becomes able to easily determine whether to charge the receiving device 20, whether to start the examination in this state, or whether to use another receiving device 20 depending on situations. Therefore, it becomes possible to prevent unnecessary charging operation, an excessive increase in the charging time, and delays in starting examinations, enabling to perform examinations efficiently.

Furthermore, conventionally, the receiving device 20 is stored while the battery 28 is maintained at a full charge level at all times so that the receiving device 20 can be used for any examination item at any time. Therefore, the battery is quickly deteriorated due to the repeated charging and discharging. In contrast, according to the first embodiment, the battery 28 is charged by an amount needed according to an examination item. Therefore, it becomes possible to prevent unnecessary charging and discharging of the battery 28, enabling to increase the lifetime of the battery 28.

First Modified Example

A first modified example of the first embodiment of the present invention will be described.

The estimated examination time corresponding to an examination item may be set independently by a user, instead of a statistically calculated general value. Specifically, setting examples (1) to (3) below may be employed.

(1) Results of examinations performed by the capsule endoscope inspection system 1 are accumulated in the storage unit 33 of the information management apparatus 30, and a statistic based on the results of the examinations (measured values of examination times) is used as an estimated examination time. For example, an average value or a mode value of examination times obtained from pieces of data on 100 people subjected to small intestine examinations is used as the estimated examination time.

(2) If the subject 2 to be examined has been subjected to a capsule endoscopic examination in the past, it may be possible to calculate an estimated examination time based on a result of the past examination (a measured value of an examination time). For example, it may be possible to use an average value or a mode value of examination times of multiple past examinations as the estimated examination time. Alternatively, it may be possible to employ an examination time of a previous examination as it is as the estimated examination time.

(3) If the subject 2 to be examiner has not been subjected to a capsule endoscopic examination in the past, it may be possible to calculate an estimated examination time based on a result of an examination (a measured value of an examination time) that is performed on a subject whose physical characteristic, such as an age or a physical build, are similar to those of the subject 2. For example, it may be possible to extract multiple subjects whose ages or physical builds are similar to that of the subject 2 from results of past examinations accumulated in the information management apparatus 30, and employ, as the estimated examination time, an average value or a mode value of examination times of examinations performed on the extracted subjects. Alternatively, it may be possible to acquire a result of an examination performed on a subject whose age or physical build is similar to that of the subject 2 from an apparatus other than the information management apparatus 30.

Second Modified Example

A second modified example of the first embodiment of the present invention will be described.

As explained in the above described first modified example, if the estimated examination time is set based on a statistic or results of past examinations, it is preferable to add a certain margin. Specifically, the estimated examination time calculated based on the statistic or the results of the past examinations may be increased by, for example, 10% or a certain time such as 1 hour. Accordingly, even if an examination time increases, it becomes possible to reduce a risk of interruption of an examination due to empty charge in the battery 28.

Third Modified Example

A third modified example of the first embodiment of the present invention will be described.

In some cases, even when the current remaining capacity of the battery 28 of the receiving device 20 is smaller than the necessary remaining capacity (Step S202: No in FIG. 7), an examination may be performed by necessity in an emergency situation or the like. For such occasions, it may be possible to display a current charging status or the like on the display device 30a, and display works or operation that the user needs to perform to complete an examination on the display device 30a. Specifically, it is preferable to display, on the display device 30a, an alert message for avoiding use of the playback view function in order to prevent consumption of the battery 28 of the receiving device 20. Alternatively, it may be possible to display a message for administering a peristaltic movement stimulator to the subject 2 in order to accelerate the movement of the capsule endoscope 10.

Even when the current remaining capacity of the battery 28 is equal to or greater than the necessary remaining capacity, if a margin of the current remaining capacity with respect to the necessary remaining capacity is small, it may be possible to display the above described message on the display device 30a.

Fourth Modified Example

A fourth modified example of the first embodiment of the present invention will be described.

If it is necessary to perform an examination in an emergency situation or the like even when the current remaining capacity of the battery 28 is smaller than the necessary remaining capacity (Step S202: No), it may be possible to transmit a control signal for controlling operation of the receiving device 20 side from the information management apparatus 30 to the receiving device 20 before the receiving device 20 is initialized. Specifically, a flag for designating operation in an energy-saving mode is transmitted. In response to this, the receiving device 20 operates in the energy-saving mode in which, for example, the luminance of a screen of the display unit 25 is reduced, a playback view is disabled, or the frequency of display of in-vivo images is controlled. Therefore, it becomes possible to prevent consumption of the battery 28, enabling to increase an operating time of the receiving device 20.

Even when the current remaining capacity of the battery 28 is equal to or greater than the necessary remaining capacity, if a margin of the current remaining capacity with respect to the necessary remaining capacity is small, it may be possible to control the receiving device 20 as described above.

Second Embodiment

A second embodiment of the present invention will be described.

A configuration and operation of a capsule endoscope inspection system according to the second embodiment are, as a whole, the same as those of the first embodiment, but a method of acquiring an estimated examination time used as a reference for calculating the necessary remaining capacity of the battery 28 differs from that of the first embodiment. Specifically, in the second embodiment, the estimated examination time is calculated based on interview information on the subject 2 to be examined or information on an examination that is preliminarily performed before the capsule endoscopic examination (preliminary examination information).

Figure 12:
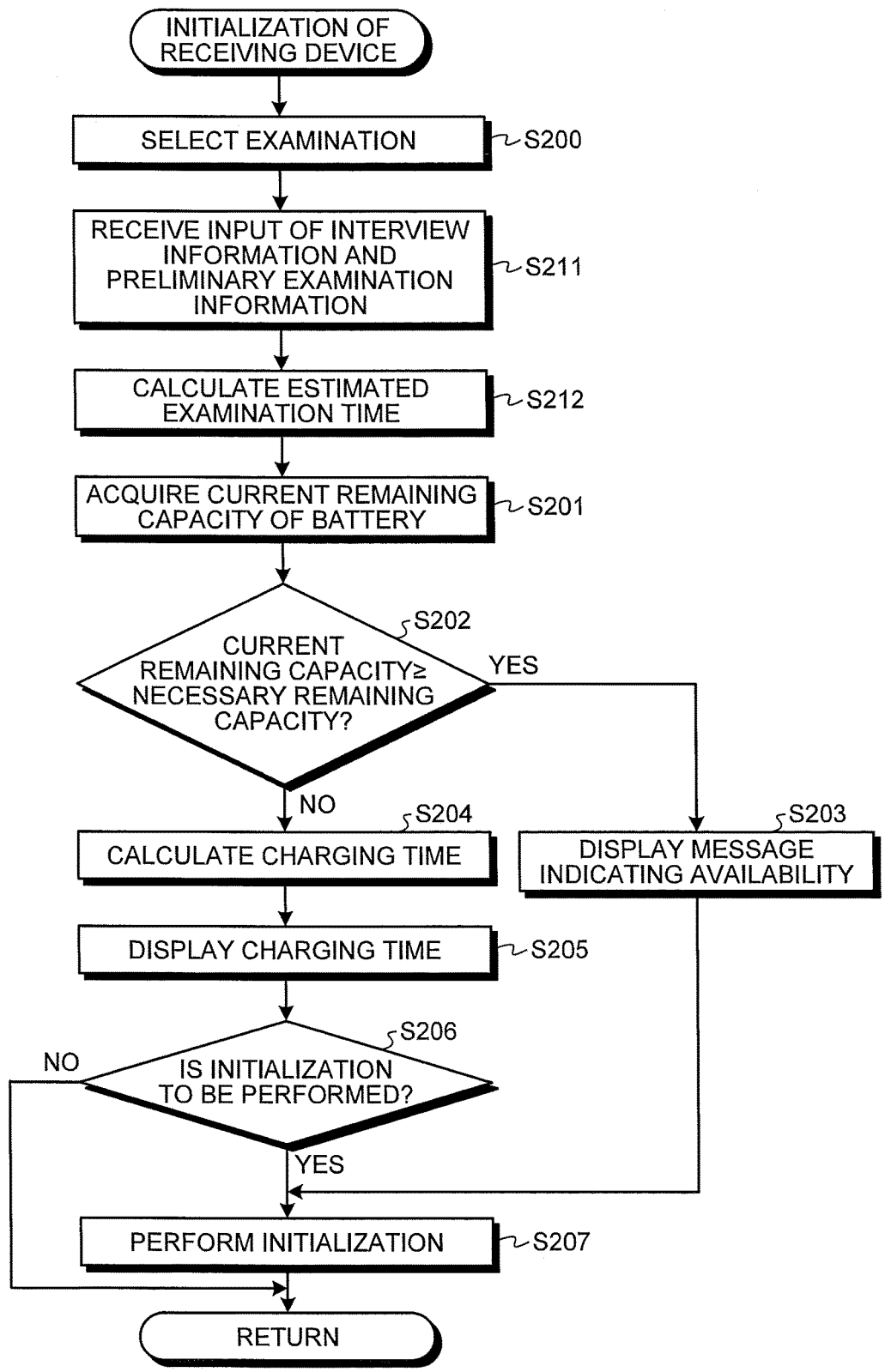
FIG. 12 is a flowchart illustrating a process of initializing a receiving device, which is performed by an information management apparatus according to a second embodiment.

FIG. 12 is a flowchart illustrating a process of initializing the receiving device 20, which is performed by the information management apparatus 30 according to the second embodiment. Step S200 illustrated in FIG. 12 is the same as that of the first embodiment.

Figure 13:
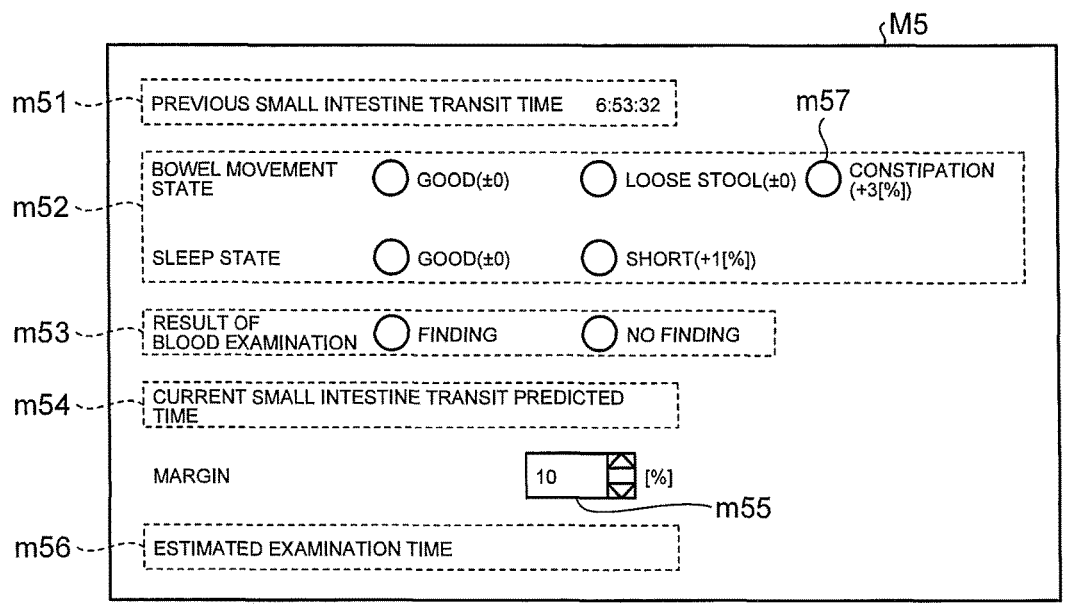
FIG. 13 is a schematic diagram illustrating an example of an input screen for inputting interview information and preliminary examination information.

At Step S211 subsequent to Step S200, the information management apparatus 30 receives input of interview information and preliminary examination information from a user. More specifically, the display controller 36c first displays, on the display device 30a, an input screen for the interview information and the preliminary examination information as illustrated in FIG. 13 for example. An input screen M5 illustrated in FIG. 13 contains a previous transit time display field m51, an interview information input field m52, a preliminary examination information input field m53, a current transit predicted time display field m54, a margin input field m55, and an estimated examination time display field m56.

The previous transit time display field m51 is an area for displaying a measured value (previous transit time) of a time taken by the capsule endoscope 10 to pass through an examination area in a previous examination performed on the subject 2. Information on the previous examination is acquired from the examination history (examination time) of the patient information stored in the patient information storage unit 33d (see FIG. 5). In FIG. 13, 6 hours, 53 minutes, and 32 seconds is displayed as a previous small intestine transit time (the examination time illustrated in FIG. 5) in association with an examination item of a small intestine examination.

The interview information input field m52 is an area for inputting a result of an interview conducted with the subject 2. Examples of an interview item include items, such as a bowel movement state (good, loose stool, constipation) and a sleep state (good, short), that influence the movement of the capsule endoscope 10 that moves by peristaltic movement. For example, when there is constipation, peristaltic movement decreases; therefore, it is assumed that the movement of the capsule endoscope 10 is slowed down. In contrast, when there is loose stool, peristaltic movement increases; therefore, it is assumed that the movement of the capsule endoscope 10 is accelerated. Furthermore, when a sleep duration is relatively short, peristaltic movement decreases; therefore, it is assumed that the movement of the capsule endoscope 10 is slowed down.

As the interview items, it may be possible to add, in addition to the above items, bowel movement states for several days before the examination, an average sleep duration over several days before the examination, a physical condition on a current day (feverish, sleepy, ill, or the like), contents of meals on several days before the examination (three meals per day, two meals per day, whether there is between-meal eating, or the like), a schedule on the day of the examination (desk work, moved around actively, or the like), a state of treatment before the examination (administration of a medicine or the like), weather, and the like.

The preliminary examination information input field m53 is an area for inputting results of preliminary examinations performed before the day of the capsule endoscopic examination. Examples of the preliminary examination item include a blood examination (whether there is a finding or there is no finding).

As options for each item in the interview information input field m52 and the preliminary examination information input field m53, radio buttons m57 are provided. The user is able to select desired options by performing pointer operation (for example, click operation) on the radio buttons m57 by using the input unit 31 to input the interview information and the preliminary examination information to the information management apparatus 30.

The current transit predicted time display field m54 is an area for displaying a predicted time (current transit predicted time) to be taken for the capsule endoscope 10 to pass through an examination area in a capsule endoscopic examination to be performed.

The margin input field m55 is an area for setting a margin to be added to the current transit predicted time calculated based on the previous transit time, the interview information, and the preliminary examination information. An initial value is set in advance as the margin, and the user is able to change the initial value to a desired value. The margin may be set as a percentage (for example, 10%) with respect to the current transit predicted time, or may be set as a fixed value (for example, 1 hour).

The estimated examination time display field m56 is an area for displaying a time obtained by adding the margin to the current transit predicted time.

Figure 14:
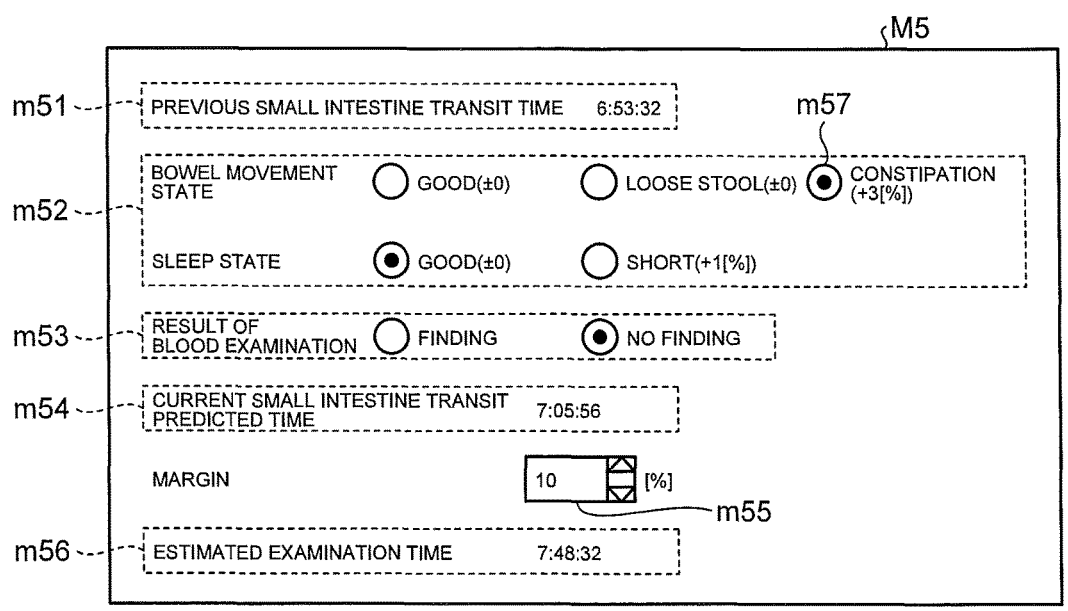
FIG. 14 is a schematic diagram illustrating a state in which the interview information and the preliminary examination information are input in the input screen illustrated in FIG. 13.

At subsequent Step S212, the calculation unit 34 corrects the previous transit time based on the information input in the input screen M5, to thereby calculate an estimated examination time. In the following, a method of calculating the estimated examination time will be described with reference to FIG. 14 by taking a small intestine examination as an example. FIG. 14 is a schematic diagram illustrating a state in which the interview information and the preliminary examination information are input to the input screen M5 illustrated in FIG. 13.

First, the calculation unit 34 adds a time, which is obtained by multiplying a coefficient set in each option in the interview information input field m52 and the preliminary examination information input field m53 by a previous small intestine transit time of 6 hours, 53 minutes, and 32 seconds, to the previous small intestine transit time to calculate the current transit predicted time. In FIG. 14, a bowel movement state of "constipation (+3%)" and a sleep state of "good (±0)" are selected. In this case, by increasing the previous small intestine transit time by 3%, the current small intestine transit predicted time of 7 hours, 5 minutes, and 56 seconds is calculated. Subsequently, the calculation unit 34 increases the current small intestine transit predicted time by a margin of 10%. Accordingly, the calculated time of 7 hours, 48 minutes, and 32 seconds is employed as the estimated examination time.

Subsequent processes after Step S201 are the same as those of the first embodiment. At Step S202, the necessary remaining capacity is set based on the estimated examination time calculated at Step S212.

As described above, according to the second embodiment, the estimated examination time is calculated based on results of past examinations on the subject 2 and a recent state of the subject 2 represented by the interview information and the preliminary examination information. Therefore, it becomes possible to set the necessary remaining capacity more realistically. Consequently, it becomes possible to perform the capsule endoscopic examination more efficiently.

Third Embodiment

A third embodiment of the present invention will be described.

In the above described first and second embodiments, it is determined whether the current remaining capacity of the battery 28 is greater or smaller than the necessary remaining capacity of the battery 28 according to the estimated examination time. However, in a more simplified manner, it may be possible to determine whether the battery 28 is in a fully charged state, and display a result of the determination to call attention of a user.

Figure 15:
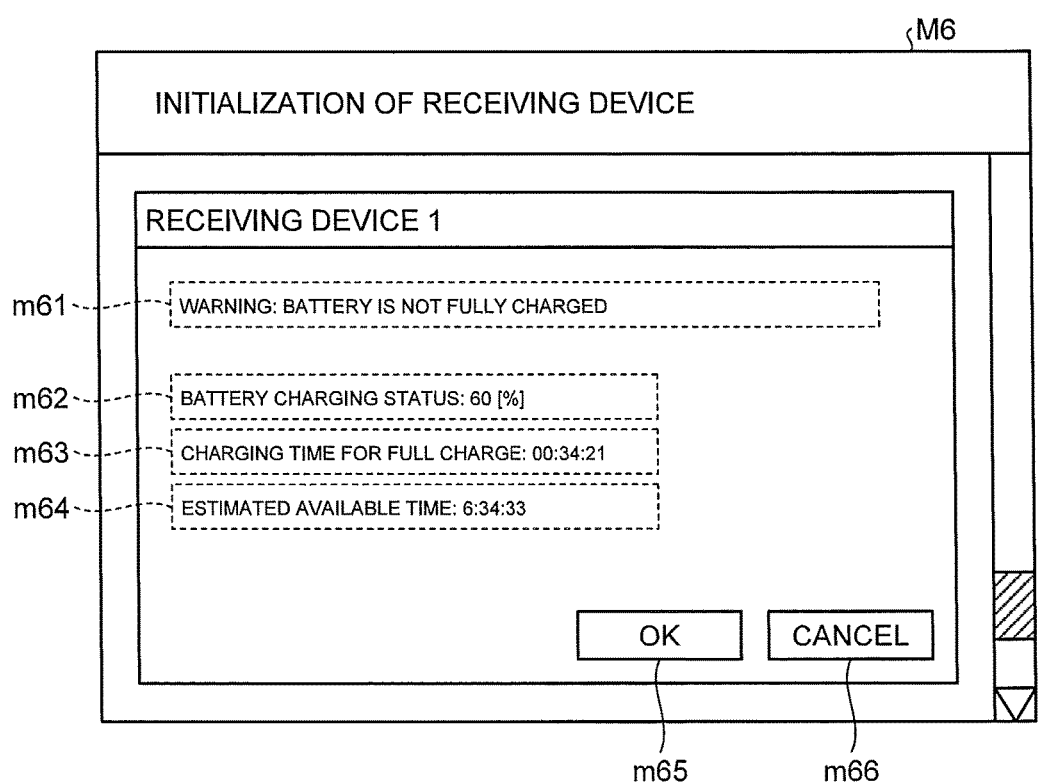
FIG. 15 is a schematic diagram illustrating an example of a screen displayed when a process of initializing a receiving device is performed by an information management apparatus according to a third embodiment.

FIG. 15 is a schematic diagram illustrating an example of a screen displayed on the display device 30a when the process of initializing the receiving device 20 is performed (see Step S2 in FIG. 6). A screen M6 illustrated in FIG. 15 contains an information display field m61, a charging status display field m62, a charging time display field m63, an estimated available time display field m64, an OK button m65, and a cancel button m66.

The information display field m61 is an area for displaying a message to give a warning to a user when the battery 28 is not fully charged.

The charging status display field m62 is an area for displaying a current charging rate (for example, 60%) of the battery 28 with respect to the fully charged state of the battery 28. The charging rate may be a rate based on the assumption that 100% indicates a state in which a new battery is fully charged, or may be a rate based on the assumption that 100% indicates a chargeable level of the current battery.

The charging time display field m63 is an area for displaying a charging time (for example, 34 minutes and 21 seconds) needed to change the status of the battery 28 from the current charging status to the fully charged status.

The estimated available time display field m64 is an area for displaying a time in which the receiving device 20 is available in the current charging status (for example, 6 hours 34 minutes 33 second).

The user refers to the information, such as the charging status, displayed in the screen M6 as described above to determine whether to initialize the receiving device 20, and inputs a result of the determination to the information management apparatus 30. Specifically, an instruction signal to perform initialization is input to the information management apparatus 30 by pointer operation on the OK button m65 using the input unit 31. Alternatively, an instruction signal to cancel initialization is input to the information management apparatus 30 by pointer operation on the cancel button m66. The information management apparatus 30 performs or cancels initialization according to the signal input from the input unit 31.

According to the above described third embodiment, when the battery 28 is not fully charged, an alert is displayed for the user. Therefore, it becomes possible to prevent interruption of the examination due to empty charge in the battery 28.

Furthermore, according to the third embodiment, the charging time needed to fully charge the battery 28 is displayed. Therefore, a user becomes able to recognize a wait time, modify an examination schedule, and perform an examination efficiently.

Moreover, according to the third embodiment, an estimated time in which the receiving device 20 is available at the current remaining capacity is displayed in addition to the above described charging time. Therefore, a user is able to easily determine whether to charge the receiving device 20, start the examination in this state, or use another receiving device 20.

As described above, according to the first to third embodiments of the present invention and the modified examples thereof, when the current remaining capacity of the battery of the receiving device is equal to or greater than the necessary remaining capacity, information indicating that the receiving device is available is displayed. When the current remaining capacity is smaller than the necessary remaining capacity, information on the charging time calculated by the calculation unit is displayed. Therefore, it becomes possible to prevent unnecessary charging operation or an excessive increase in the charging time. As a result, it becomes possible to prevent delay in starting the examination.

The present invention is not limited to the first to third embodiments and the modified examples thereof, and various inventions may be formed by appropriately combining a plurality of structural elements disclosed in the respective embodiments and modified examples. For example, formation by excluding some of the structural elements from the whole structural elements illustrated in the respective embodiments and modified examples may be made, or formation by appropriately combining the structural elements illustrated in the different embodiments and modified examples may be made. It is obvious from the above descriptions that the present invention may be modified in various forms according to a specification or the like, and various embodiments are possible without departing from the scope of the present invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An apparatus for managing a receiving device comprising: a receiver configured to receive wirelessly transmitted data from a capsule endoscope as the capsule endoscope performs an examination of a selected type; and a rechargeable battery configured to supply electric power to at least the receiver to receive the wirelessly transmitted data, the apparatus comprising:
   a processor comprising hardware, wherein the processor is configured to:
      acquire a current value of a remaining capacity of the rechargeable battery;
      access a memory configured to store, for the examination of the selected type, a necessary value of the remaining capacity of the rechargeable battery needed to complete the examination of the selected type;
      determine whether the current value of the remaining capacity of the rechargeable battery is equal to or greater than the necessary value of the remaining capacity of the rechargeable battery; and
      in response to determining that the current value of the remaining capacity of the rechargeable battery is not equal to or greater than the necessary value of the remaining capacity of the rechargeable battery:
         calculate a charging time needed to increase the remaining capacity of the rechargeable battery from the current value of the remaining capacity to the necessary value of the remaining capacity;
         calculate a predicted portion of the examination of the selected type that can be completed with the current value of the remaining capacity of the rechargeable battery; and
         control a display to display the charging time and the predicted portion of the examination of the selected type that can be completed.

2. The apparatus according to claim 1, further comprising the memory,
   wherein the memory is configured to store the necessary value of the remaining capacity wherein the necessary value is set based on a statistic of an examination time of the selected type of examination performed by the capsule endoscope.

3. The apparatus according to claim 1, further comprising the memory,
wherein the memory is configured to store:
measured values of examination times of a plurality of examinations of the selected type performed in the past; and
the necessary value of the remaining capacity, wherein the necessary value is set based on the measured values of examination times.

4. The apparatus according to claim 3, further comprising the memory,
wherein the memory is configured to store the necessary value of the remaining capacity wherein the necessary value is set based on a measured value that is extracted, from among the measured values, in accordance with an age or a physical build of a subject to be examined.

5. The apparatus according to claim 1, further comprising the memory,
wherein the memory is configured to store the necessary value of the remaining capacity wherein the necessary value is set based on a measured value of an examination time in a past examination of the selected type performed on the same subject.

6. The apparatus according to claim 5, further comprising the memory,
wherein the memory is configured to store the necessary value of the remaining capacity wherein the necessary value is set based on a value that is corrected from the measured value based on information on the same subject.

7. A system comprising:
a capsule endoscope configured to perform an examination of a selected type and to wirelessly transmit data as the capsule endoscope performs the examination of the selected type;
a receiving device comprising:
a receiver configured to receive the wirelessly transmitted data from the capsule endoscope as the capsule endoscope performs the examination of the selected type; and
a rechargeable battery configured to supply electric power to at least the receiver to receive the wirelessly transmitted data; and
a processor comprising hardware, wherein the processor is configured to:
acquire a current value of a remaining capacity of the rechargeable battery;
access a memory configured to store, for the examination of the selected type, a necessary value of the remaining capacity of the rechargeable battery needed to complete the examination of the selected type;
determine whether the current value of the remaining capacity of the rechargeable battery is equal to or greater than the necessary value of the remaining capacity of the rechargeable battery; and
in response to determining that the current value of the remaining capacity of the rechargeable battery is not equal to or greater than the necessary value of the remaining capacity of the rechargeable battery:
calculate a charging time needed to increase the remaining capacity of the rechargeable battery from the current value of the remaining capacity to the necessary value of the remaining capacity;
calculate a predicted portion of the examination of the selected type that can be completed with the current value of the remaining capacity of the rechargeable battery; and
control a display to display the charging time and the predicted portion of the examination of the selected type that can be completed.

8. The apparatus according to claim 1, further comprising the memory,
wherein the examination of the selected type is an examination of a selected organ, and
wherein the memory is configured to store, for the examination of the selected organ, the necessary value of the remaining capacity of the rechargeable battery needed to complete the examination of the selected organ.

9. A computer-readable storage device storing instructions for managing a receiving device comprising: a receiver configured to receive wirelessly transmitted data from a capsule endoscope as the capsule endoscope performs an examination of a selected type; and a rechargeable battery configured to supply electric power to at least the receiver to receive the wirelessly transmitted data, wherein the instructions cause a computer to perform processes comprising:
acquiring a current value of a remaining capacity of the rechargeable battery;
accessing a memory configured to store, for the examination of the selected type, a necessary value of the remaining capacity of the rechargeable battery needed to complete the examination of the selected type;
determining whether the current value of the remaining capacity of the rechargeable battery is equal to or greater than the necessary value of the remaining capacity of the rechargeable battery; and
in response to determining that the current value of the remaining capacity of the rechargeable battery is not equal to or greater than the necessary value of the remaining capacity of the rechargeable battery:
calculating a charging time needed to increase the remaining capacity of the rechargeable battery from the current value of the remaining capacity to the necessary value of the remaining capacity;
calculating a predicted portion of the examination of the selected type that can be completed with the current value of the remaining capacity of the rechargeable battery; and
controlling a display to display the charging time and the predicted portion of the examination of the selected type that can be completed.

* * * * *